US010317394B2

(12) United States Patent
Piazza et al.

(10) Patent No.: US 10,317,394 B2
(45) Date of Patent: Jun. 11, 2019

(54) SENSITIZED CULTURED CELLS FOR BOTULINUM TOXIN CHARACTERIZATION (71) Applicant: BIOMADISON, INC., Del Mar, CA (US)

(72) Inventors: Timothy M. Piazza, McFarland, WI (US); Ward C. Tucker, Monona, WI (US)

(73) Assignee: BIOMADISON, INC., Del Mar, CA (US)

( * ) Notice: Subject to any disclaimer, the term of this patent is extended or adjusted under 35 U.S.C. 154(b) by 211 days.

(21) Appl. No.: 15/051,409

(22) Filed: Feb. 23, 2016

(65) Prior Publication Data
US 2016/0223524 A1    Aug. 4, 2016

Related U.S. Application Data (63) Continuation of application No. 13/733,803, filed on Jan. 3, 2013, now Pat. No. 9,303,285, which is a continuation-in-part of application No. 13/485,537, filed on May 31, 2012, now Pat. No. 9,274,121, which is a continuation of application No. 61/582,940, filed on Jan. 4, 2012, which is a continuation of application No. 61/492,237, filed on Jun. 1, 2011.

(51) Int. Cl.
C12Q 1/37 (2006.01)
G01N 33/50 (2006.01)
G01N 33/58 (2006.01)
G01N 33/569 (2006.01)

(52) U.S. Cl.
CPC .......... *G01N 33/5014* (2013.01); *C12Q 1/37* (2013.01); *G01N 33/56911* (2013.01); *G01N 33/582* (2013.01); *G01N 2333/33* (2013.01); *G01N 2333/952* (2013.01)

(58) Field of Classification Search
None
See application file for complete search history.

(56) References Cited

U.S. PATENT DOCUMENTS

| | | | |
|---|---|---|---|
| 7,183,066 B2 | 2/2007 | Fernandez-Salas et al. | |
| 7,208,285 B2 | 4/2007 | Steward et al. | |
| 8,137,924 B2 | 3/2012 | Chapman et al. | |
| 2004/0191887 A1 | 9/2004 | Chapman et al. | |
| 2006/0134722 A1 | 6/2006 | Chapman et al. | |
| 2009/0076019 A1 | 3/2009 | Tyers et al. | |
| 2009/0191583 A1 | 7/2009 | Fernandez-Salas et al. | |
| 2010/0278745 A1 | 11/2010 | Lange et al. | |
| 2011/0033866 A1 | 2/2011 | Fish et al. | |

FOREIGN PATENT DOCUMENTS

| | | |
|---|---|---|
| WO | 2004/031355 A2 | 4/2004 |
| WO | 2004/031355 A3 | 4/2004 |
| WO | 2005/076785 A2 | 8/2005 |
| WO | 2005/076785 A3 | 8/2005 |
| WO | 2009/114748 A1 | 9/2009 |
| WO | 2010/090677 A1 | 8/2010 |

OTHER PUBLICATIONS

Ronca F et al. 1-(5-Isoquinolinesulfonyl)-2-methylpiperazine Induces Apoptosis in Human Neuroblastoma Cells, SH-SY5Y, through a p53 dependent pathway. 1997. The Journal of Biological Chemistry. vol. 272, No. 7: 4252-4260. (Year: 1997).*
Berney, C. et al., "FRET or No FRET: A Quantitative Comparison", Biophysical Journal, 2003, pp. 3992-4010, vol. 84, No. 6.
Capek, P. et al., "Sensing the Deadliest Toxin: Technologies for Botulinum Neurotoxin Detection", Toxins, 2010, pp. 24-53, vol. 2.
Clegg, R.M. et al., "How Can One Choose the Best Method for Measuring FRET in a Microscope with My Biological System?", Microscopy and Micronanalysis, 2005, pp. 272-273, vol. 11 (Supplement 2).
Fang, H. et al., "A yeast assay probes the interaction between botulinum neurotoxin serotype B and its SNARE substrate", Proceedings of the National Academy of Sciences, May 2, 2006, pp. 6958-6963, vol. 103, No. 18.
Hunt, T. et al., "Characterization of SNARE Cleavage Products Generated by Formulated Botulinum Neurotoxin Type-A Drug Products", Toxins, 2010, pp. 2189-2212, vol. 2.
Patent Cooperation Treaty, "Notification of Transmittal of the International Search Report and the Written Opinion of the International Searching Authority or the Declaration", PCT/US13/20169, dated Mar. 14, 2013.
Ruge, D.R. et al., "Detection of six serotypes of botulinum neurotoxin using fluorogenic reporters", Analyitical Biochemistry, 2011, pp. 200-209, vol. 411.
Sheng Chen and Joseph T. Barbieri, "Protein Synthesis, Post-Translation Modification, and Degradation: Unique Substrate Recognition by Botulinum Neurotoxins Serotypes A and E", The Journal of Biological Chemistry, Downloaded on Dec. 9, 2013, vol. 281, No. 16, pp. 10906-10911.

(Continued)

*Primary Examiner* — Paul J Holland
(74) *Attorney, Agent, or Firm* — Fish IP Law, LLP (57) ABSTRACT

Apparatus, systems and methods can provide improved detection of botulinum neurotoxins. In one aspect an isoquinolynyl compound can be used to enhance the sensitivity of both Förster resonance energy transfer (FRET) and non-FRET cell-based assays. In another aspect, non-FRET assays and constructs utilize a reporter that is not coupled with the second fluorophore in a manner that produces significant FRET. In that subject matter an environment cell can include an enzyme that facilitates degradation of the reporter significantly faster after the cleavage than before the cleavage, and presence of the Botulinum toxin correlates with reduction of the signal from a baseline signal. Where the environment is a cell, the cell can advantageously express both the construct that includes the reporter, and an enzyme that facilitates the degradation.

11 Claims, 7 Drawing Sheets

(56) References Cited

OTHER PUBLICATIONS

Sheng Chen and Joseph T. Barbieri, "Protein Synthesis, Post-Translation Modification, and Degradation: Multiple Pocket Recognition of SNAP25 by Botulinum Neurotoxin Serotype E", The Journal of Biological Chemistry, Downloaded on Dec. 9, 2013, vol. 282, No. 35, pp. 25540-25547.
Chen et al., "Enzyme Catalysis and Regulation: Mechanism of Substrate Recognition by Botulinum Neurotoxin Serotype A", The Journal of Biological Chemistry, Downloaded on Dec. 9, 2013, vol. 282, No. 13, pp. 9621-9627.
Chen et al., "Substrate Recognition of VAMP-2 by Botulinum Neurotoxin B and Tetanus Neurotoxin", The Journal of Biological Chemistry, Downloaded on Dec. 9, 2013, vol. 283, No. 30, pp. 21153-21159.
Kalb et al., "Different Substrate Recognition Requirements for Cleavage of Synaptobrevin-2 by Clostridium baratii and Clostridium botulinum Type F Neurotoxins", Applied and Environmental Microbiology, Feb. 2011, vol. 77, No. 4, pp. 1301-1308.
Pellizzari et al., "Structural Determinants of the Specificity for Synaptic Vesicle-associated Membrane Protein/Synaptobrevin of Tetanus and Botulinum Type B and G Neurotoxins", The Journal of Biological Chemistry, vol. 271, No. 34, Aug. 23, 1996, pp. 20353-20358.
Pellizzari et al., "The interaction of synaptic vesicle-associated membrane protein/synaptobrevin with botulinum neurotoxins D and F", Federation of European Biochemical Societies Letters 409 (1997), pp. 339-342.
Schiavo et al., "Botulinum Neurotoxin Type C Cleaves a Single Lys-Ala Bond within the Carboxyl-terminal Region of Syntaxins", The Journal of Biological Chemistry, vol. 270, No. 18, May 5, 1995, pp. 10566-10570.

\* cited by examiner

FIG. 1A

| | EC$_{50}$ (pM) |
|---|---|
| ● Control | ---- |
| ◆ 1 mM H7 | 79.0 |
| ▼ 0.1mM H7 | ---- |

FIG. 1B

● Control Curve (DMBO)
◆ 1 uM Cal C
▼ 0.1uM Cal C

FIG. 1C

● Control Curve (DMBO)
◆ 1 mM IBMX
▼ 0.1mM IBMX

| [H7] | EC$_{50}$ (pM) |
|---|---|
| ● 0 mM | ---- |
| ◆ 0.1 mM | ---- |
| ▼ 0.25 mM | 890.4 |
| ▲ 0.5 mM | 644.5 |
| ■ 0.75 mM | 353.2 |
| ○ 1 mM | 227.8 |

| Pre-treatment Time | EC$_{50}$ (pM) |
|---|---|
| ● 3 hr | 460.5 |
| ◆ 6 hr | 370.4 |
| ▼ 12 hr | 355.0 |
| ▲ 24 hr | 287.0 |

FIG. 4A

| | EC$_{50}$ (pM) |
|---|---|
| ● Holotoxin | 130.1 |
| ◆ Light Chain | ---- |

FIG. 4B

| | EC$_{50}$ (pM) |
|---|---|
| ● Holotoxin | 256.9 |
| ◆ HcR/A | ---- |

FIG. 5

| | EC$_{50}$ (pM) |
|---|---|
| ● Control | ---- |
| ◆ Sigma | 134.7 |
| ▼ ToCris | 145.2 |
| ▲ Toronto | 115.4 |

SENSITIZED CULTURED CELLS FOR BOTULINUM TOXIN CHARACTERIZATION

PRIORITY CLAIM

This application is a continuation of U.S. patent application Ser. No. 13/733,803, filed Jan. 3, 2013, issued as U.S. Pat. No. 9,303,285, which claims priority to U.S. Provisional Patent Application No. 61/582940, filed Jan. 4, 2012 and is a continuation in part of U.S. patent application Ser. No. 13/485537, filed May 31, 2012, and issued as U.S. Pat. No. 9,274,121, which claims the benefit of U.S. Provisional Application No. 61/492,237, filed Jun. 1, 2011, the disclosures of which are incorporated herein by reference in their entirety. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is characterization of Botulinum Neurotoxins (BoNTs).

BACKGROUND

Botulinum Neurotoxins are the most lethal substances known, and depending on the scrotype, the estimated human lethal dose ranges from 1 to 3 ng toxin per kg body weight. Due to their ease of purification and high potency, BoNTs pose a real and potential threat for use as bioweapons. Further, BoNTs are increasing used for cosmetic and therapeutic purposes. Currently, the majority of BoNT detection and potency measurements completed in government and industrial laboratories are done using animal-based assays that suffer from high costs and poor accuracy.

The primary advantage of using cell-based assays (CBAs) for BoNT potency measurements is that CBA systems closely mimic the individual physiologic steps that occur in neurons during intoxication. BoNTs are zinc-dependent endopeptidases composed of a heavy chain, responsible for neuron-specific receptor binding and cell entry, and a catalytic light chain responsible for synaptic protein cleavage. Upon entry into neurons, the BoNTs specifically disrupt the protein machinery responsible for fusion of synaptic vesicles with the plasma membrane, thereby inhibiting neurotransmitter release into the post-synaptic junction. Because all physiologic steps must be accounted for in CBAs, most assays fail to meet the sensitivity requirements of BoNT activity measurement.

The employment of established, stable model cell lines for the detection of BoNTs have recently been described, however, past CBAs fail to meet the sensitivity requirements for the quantification of pharmaceutical preparations of BoNT or the detection of BoNT in clinical samples. Presumably, current established model cell lines lack critical neuronal characteristics required for efficient BoNT uptake. A recent solution to increasing BoNT sensitivity is the use of mouse embryonic stem cells (mESCs). Because these cells can be terminally differentiated into neurons they are more sensitive to BoNT treatment. A major drawback to this method, though, is the multiple weeks required to fully differentiate mESCs.

Thus, there is an urgent need to development cell based assays for assessing and quantifying the potency of BoNT-containing samples for bioweapon defense, food borne illness, and therapeutic purposes.

SUMMARY OF THE INVENTION

The inventive subject matter is directed to a cultured cell that is susceptible to intoxication by a Botulinum neurotoxin. Susceptibility of the cell to such a neurotoxin is enhanced by contacting the cell with a protein kinase C (PKC) inhibitor. In preferred embodiments the PKC inhibitor is an isoquinolynyl compound, for example 1-(5-isoquinolinylsulfonyl)-2-methylpiperazine dichloride (H7). In some embodiments, inhibition of PKC with an isoquinolynyl compound such as 1-(5-isoquinolinylsulfonyl)-2-methylpiperazine dichloride (H7), significantly enhances the intoxication of the cell by a botulinum toxin to produce a sensitized cell.

Also contemplated is optimization of a cell culture medium containing B27 for contact with such a sensitized cell and a Botulinum toxin. Essentially, the osmolarity of the culture media can be adjusted with respect to specific Botulinum toxin preparations by modifying sodium chloride concentration to, for example, optimize functionality with Botulinum toxin preparations that include about 15.4 mM and/or carbohydrate concentrations to up to 0.5% and/or human serum albumin concentrations to up to 0.1%.

BRIEF DESCRIPTION OF THE DRAWINGS

FIG. 1A depicts the effect of H7. FIG. 1B depicts the effect of calphostin. FIG. 1C depicts the effect of IBMX. FIG. 1D depicts the effects of db-cAMP. FIG. 1E depicts the effects of 8-Br-cAMP.

FIGS. 2A and 2B are graphs showing that the H7 effect is dose dependent, and does not affect cell viability.

FIGS. 4A and 4B are graphs showing that 1) only holotoxin (complete BoNT/A) but not light-chain (BoNT/A fragment) elicits a response in the BoCell™ assay and 2) BoNT/A activity can be blocked by the addition of HcR/A which competes for cellular receptors. Thus, BoNT/A responses in the assay occur through natural mechanisms. FIG. 1B shows the effect of the HcR/A competitor on BoNT/A holotoxin activity.

DETAILED DESCRIPTION

In preferred embodiments, the investigational substance is a Botulinum toxin (BoNT), and the cleavage sequence is appropriately matched with the investigational substance. For example, the BoNT/A, E, and C cleave SNAP-25, and BoNT/B, D, F, G cleave synaptobrevin (Syb), at single but different sites. BoNT/C also cleaves syntaxin in addition to SNAP-25.

Cleavage Sequence(s)

Contemplated cleavage site sequences can advantageously comprise (a) a SNARE protein, motif, or mutein. "Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

Transfected Cells

Hybrid protein(s) that are formed in the transfected cells preferably include a transmembrane domain, which tends to locate to intracellular vesicles for BoNT/B, D, F, and G, and thereby present a vesicle-bound substrate. Heavy chain-mediated endocytosis of the BoNT into the transfected cell is followed by presentation of the light chain on the outer surface of the vesicle, allowing the protease activity of the light chain to cleave the cleavage sequence of the hybrid protein(s), thus cleaving the reporter-containing portion, which then is destroyed or degraded to reduce the signal being tested. Full-length Syb, for example, contains 116 amino acids, and is localized to vesicles through a single transmembrane domain.

Hybrid protein(s) that are formed in the transfected cells preferably include a transmembrane domain, which tends to locate to the plasma membrane for BoNT/A, C, and E. In some contemplated assays, the membrane-anchoring domain comprises a fragment that contains a palmitoylation site. Suitable membrane-anchoring domains are described, for example, in US 20060134722 to Chapman.

While it is especially preferred that the transmembrane domain is the transmembrane domain of synaptobrevin, mutations (e.g., transitions, transversions, insertions, deletions, inversions, etc.) thereof, and even non-synaptobrevin transmembrane domains are also deemed suitable for use herein. Similarly, it should be appreciated that the transmembrane domain may also be replaced by another polypeptide moiety that allows at least temporary anchoring of the hybrid protein to a membrane such that the remainder of the hybrid protein is exposed to the cytosol.

With respect to the transfected cells expressing the hybrid protein it is generally preferred that the cell is stably transfected. Nevertheless, transient transfection is also contemplated. It is still further typically preferred that the transfected cell is a neuronal cell. However, numerous other non-neuronal cells (including mammalian, rodent, and insect cells, and even yeast and bacterial cells) are also contemplated herein. Most typically, the cells will constitutively express the hybrid protein(s) are therefore under appropriate regulatory elements. In alternative aspects, the expression may also be induced.

According to a preferred embodiment, a recombinant nucleic acid molecule, preferably an expression vector, encoding a BoNT substrate polypeptide and a suitable reporter is introduced into a suitable host cell. An ordinarily skilled person can choose a suitable expression vector, preferably a mammalian expression vector, and will recognize that there are enormous numbers of choices. For example, the pcDNA series of vectors, such as pCI and pSi (from Promega, Madison, Wis.), CDM8, pCeo4. Many of these vectors use viral promoters. Preferably, inducible promoters are used, such as the tet-off and tet-on vectors from Clontech (Mountain View, Calif.).

Many choices of cell lines are suitable as the host cell. Preferably, the cell is of a type in which the respective BoNT exhibits its toxic activities. In other words, the cells preferably display suitable cell surface receptors, or otherwise allow the toxin to be translocated into the cell sufficiently efficiently, and allow the toxin to cleave the suitable substrate polypeptide. Specific examples include primary cultured neurons (cortical neuron, hippocampal neuron, spinal cord motor neuron, etc); PC12 cells or derived PC12 cell lines; primary cultured chromaffin cells; several cultured neuroblastoma cell lines, such as murine cholinergic Neuro 2a cell line, human adrenergic SK-N-SH cell line, and NS-26 cell line. See e.g. Foster and Stringer (1999), Genetic Regulatory Elements Introduced Into Neural Stem and Progenitor Cell Populations, Brain Pathology 9: 547-567.

The coding region for the reporter/cleavage site construct is under the control of a suitable promoter. Depending on the types of host cells used, many suitable promoters are known and readily available in the art. Such promoters can be inducible or constitutive. A constitutive promoter may be selected to direct the expression of the desired polypeptide. Such an expression construct may provide additional advantages since it circumvents the need to culture the expression hosts on a medium containing an inducing substrate. Examples of suitable promoters would be LTR, SV40 and CMV in mammalian systems; *E. coli* lac or trp in bacterial systems; baculovirus polyhedron promoter (polh) in insect systems and other promoters that are known to control expression in eukaryotic and prokaryotic cells or their viruses. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), .alpha.-amylase (amy), amyloglucosidase (AG—from the glaA gene), acetamidase (amdS) and glyceraldehyde-3-phosphate dehydrogenase (gpd) promoters. Examples of strong yeast promoters are those obtainable from the genes for alcohol dehydrogenase, lactase, 3-phosphoglycerate kinase and triosephosphate isomerase. Examples of strong bacterial promoters include SPO2 promoters as well as promoters from extracellular protease genes.

Hybrid promoters may also be used to improve inducible regulation of the expression construct. The promoter can additionally include features to ensure or to increase expression in a suitable host. For example, the features can be conserved regions such as a Pribnow Box or a TATA box. The promoter may even contain other sequences to affect (such as to maintain, enhance or decrease) the levels of expression of the nucleotide sequence. For example, suitable other sequences include the Sh1-intron or an ADH intron. Other sequences include inducible elements-such as temperature, chemical, light or stress inducible elements. Also, suitable elements to enhance transcription or translation may be present. An example of the latter element is the TMV 5' signal sequence (see Sleat, 1987, Gene 217: 217-225; and Dawson, 1993, Plant Mol. Biol. 23: 97).

The expression vector may also contain sequences which act on the promoter to amplify expression. For example, the SV40, CMV, and polyoma cis-acting elements (enhancer) and a selectable marker can provide a phenotypic trait for selection (e.g. dihydrofolate reductase or neomycin resistance for mammalian cells or amplicillin/tetracycline resistance for E. coli). Selection of the appropriate vector containing the appropriate promoter and selection marker is well within the level of those skilled in the art.

Preferably, the coding region for the construct is under the control of an inducible promoter. In comparison to a constitutive promoter, an inducible promoter is preferable because it allows for suitable control of the concentration of the reporter in the cell, therefore the measurement of changes in signals are greatly facilitated.

For example, expression can be controlled using the Tet-on & Tet-off system Clontech (Mountain View, Calif.). Under the control of this promoter, gene expression can be regulated in a precise, reversible and quantitative manner. Briefly, for Tet-on system, the transcription of downstream gene only happens when doxycycline is present in the culture medium. After the transcription for a certain period of time, one can change culture medium to deplete doxycycline, thus, stop the synthesis of new reporter proteins. Therefore, there is no background from newly synthesized reporter proteins, and one may be able to see a faster change after toxin treatment.

Fluorescent Analysis

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy emission can be carried out with an argon ion laser, a high intensity mercury (Hg) arc lamp, a fiber optic light source, or other high intensity light source appropriately filtered for excitation in the desired range. It will be apparent to those skilled in the art that excitation/detection means can be augmented by the incorporation of photomultiplier means to enhance detection sensitivity. For example, the two photon cross correlation method may be used to achieve the detection on a single-molecule scale (see e.g. Kohl et al., Proc. Nat'l. Acad. Sci., 99:12161, 2002).

Sensitizer

In a particular embodiment, inhibitor 1-(5-isoquinolinyl-sulfonyl)-2-methylpiperazine dichloride (H7) significantly enhances the sensitivity of the BoCell™ model cell line to botulinum neurotoxin type A (BoNT/A).

Pretreatment of the BoCell™ modified neuroblastoma cells with H7 caused rapid increases in both neurite length and neurite number per cells. The H7 effect was both time and dose-dependent with maximal effects seen with 1 mM H7 treatment. Further, this phenotypic change could be "rescued" by removal of the H7. Lastly, pretreatment of cells with H7 significantly increased the sensitivity of these cells to BoNT/A treatment as measured by SNAP-25 reporter cleavage.

H7 also inhibits cAMP and cGMP-dependent kinases, though pretreatment of cells with the drug HA1004, a selective inhibitor of cAMP and cGMP kinases failed to induce morphologic changes in neuroblastoma cells, suggesting the effect is specific to PKC inhibition (1990, JBC paper). On the other hand, other molecules that are known neuronal cell differentiators, including some inhibitors of PKA and PKC, do NOT increase the sensitivity of the BoCell™ Assay. The increased sensitivity was not seen with other drugs previously shown to induce neurite formation: Calphostin C, IBMX, dibutyryl-cAMP, and 8-Bromoadenosine-cAMP.

It is thus contemplated that inhibition of specific PKC isoforms with selective isoquinolynyl analogues and other drugs may infer similar increases in BoNT/A sensitivity in established model cell lines by inducing neurite formation.

It is also contemplated that the culture media can include one or both of H7 and B27, and that the osmolarity of the culture media can be modified to optimize effectiveness with respect to specific Botulinum toxins, especially those in Table 1. Osmolarity can be adjusted in according to known principles, including especially modifying the salt and/or sugar content. As used herein, the term "optimization" means taking steps to improve a desired result, which may or may not actually achieve the best possible result.

TABLE 1

Excipient formulations of BoNT/A-based pharmaceuticals. Botox ® is manufactured by Allergan Inc. (Irvine, CA), Dysport ® by Ipsen (France), and Xeomin ® by Merz GmbH (Germany).

| Therapeutic | Active ingredient per vial | Supplied form | Excipients per vial | Content concentrations in a 1 ml |
|---|---|---|---|---|
| Botox ® | 100 U BoNT/A | Lyophilized powder | 0.5 mg HSA, 0.9 mg NaCl | 100 U BoNT/A, 0.05% HSA, 15.4 mM NaCl |
| Dysport ®/ Reloxin ® | 500 U BoNT/A | Lyophilized powder | 125 µg HSA, 2.5 mg lactose | 500 U BoNT/A, 0.0125% HSA, 0.25% lactose |
| Xeomin ® | 100 U BoNT/A | Lyophilized powder | 1 mg HSA, 4.7 mg sucrose | 100 U BoNT/A, 0.1% HSA, 0.47% sucrose |

Sensitizer Experimental Results

Our finding is that treatment of our BoCell™ cells with the compound H7 increases the sensitivity of our BoCell™ assay. From a methods standpoint, the possible technological advantages of H7 treatment include:

1. Reduced assay times. With H7 treatment, we get BoCell™ BoNT/A sensitivities after 24 hours of BoNT/A treatment that are equivalent to 72 hour BoNT/A treatments with our current assay conditions. An assay time reduction of 48 hours.
2. Overall increase in assay sensitivity. Using H7 we can increase the sensitivity of the assay by 0.5 log-1.0 log with a 48 hour BoNT/A treatment compared to our current assay conditions. We expect that further increases in sensitivity with assay optimization.
3. Increase neuronal cell sensitivity to other BoNT serotypes. We are currently testing this.

It is thus contemplated that use of the compounds contemplated herein can increase the sensitivity of the assay by at least 0.5 log, at least 0.6 log, at least 0.7 log, at least 0.8 log, at least 0.9 log and at least 1.0. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

FIGS. 1A to 1E, 2A, 2B, 3, 4A, 4B, 5, and 6 show data generated using H7.

In FIGS. 1A, 1B, 1C, 1D, and 1E, BoCells were plated, and pre-treated for 24 hr with A) H7 (FIG. 1A), B) Calphostin C (FIG. 1B), C) IBMX (FIG. 1C), D) dibutyryl-cyclic AMP (db-cAMP) (FIG. 1D), or E) 8-brom o-cyclic AMP (8-Br-cAMP) (FIG. 1E) at the indicated concentration. Control cells were treated with vehicle equivalent to the highest drug concentration tested. After pre-treatment, BoCells were treated with BoNT/A containing indicated drug concentration for an additional 24 hr. The assay response was collected by reading the emission at 485 and 535 nm using a Tecan™ Infinite 500 series microplate reader. Emission ratios (YFP/CFP) were plotted as a function of BoNT/A concentration. Data represent mean±standard deviation of the mean of samples run in triplicate.

Figure 1A:
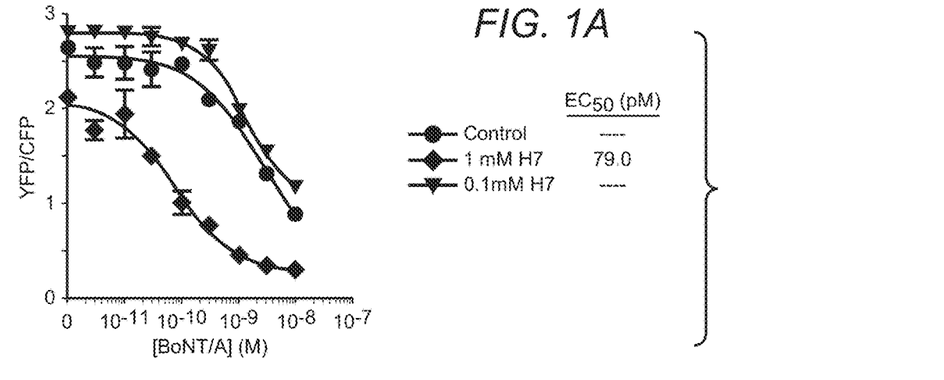
FIGS. 1A, 1B, 1C, 1D, and 1E are graphs showing that H7 treatment, but not calphostin, IBMX, db-cAMP, or 8-Br-cAMP treatment, cause an increase in BoCell™ Assay sensitivity.
Figure 1B:
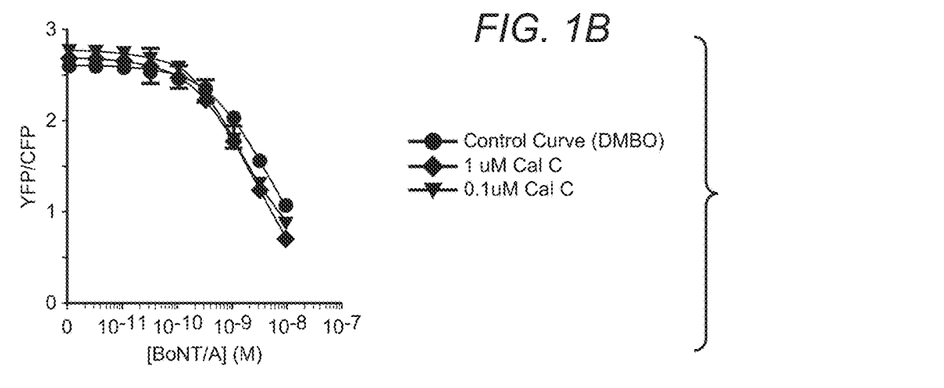
Figure 1C:
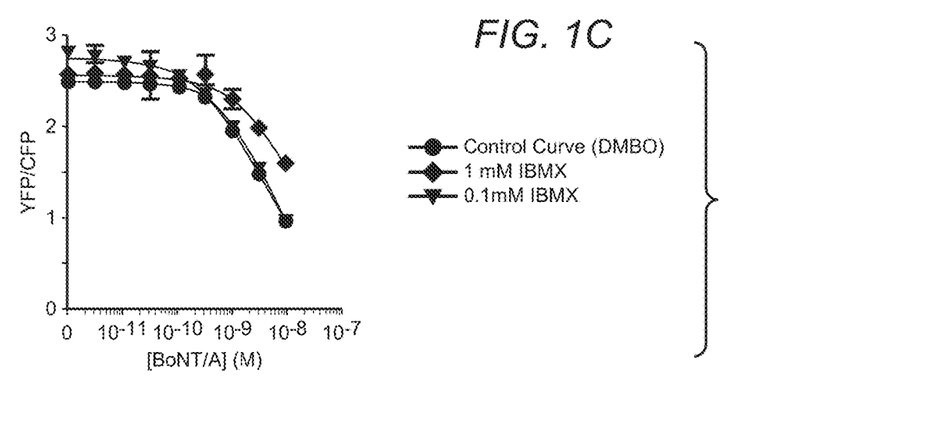
Figure 1D:
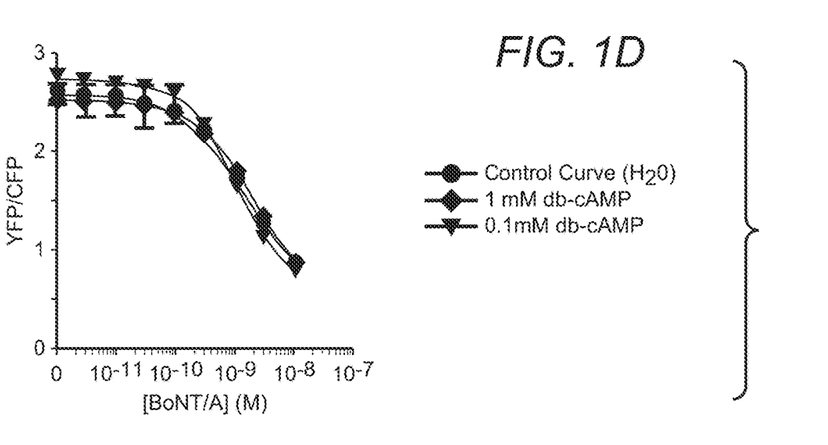
Figure 1E:
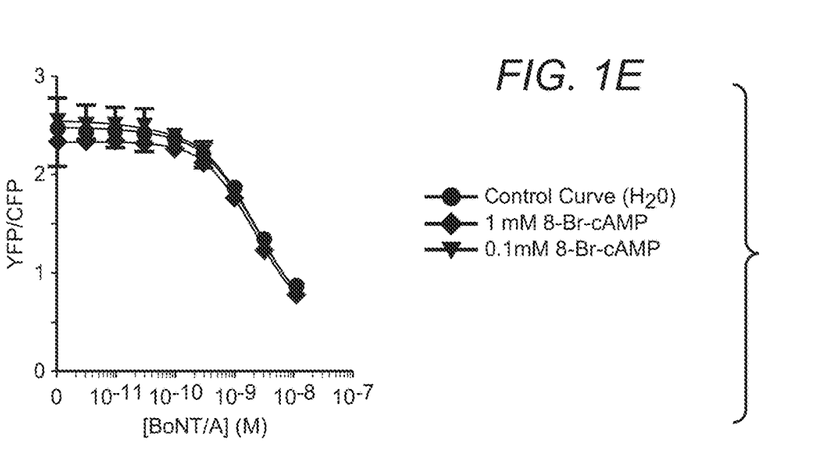
Figure 2A:
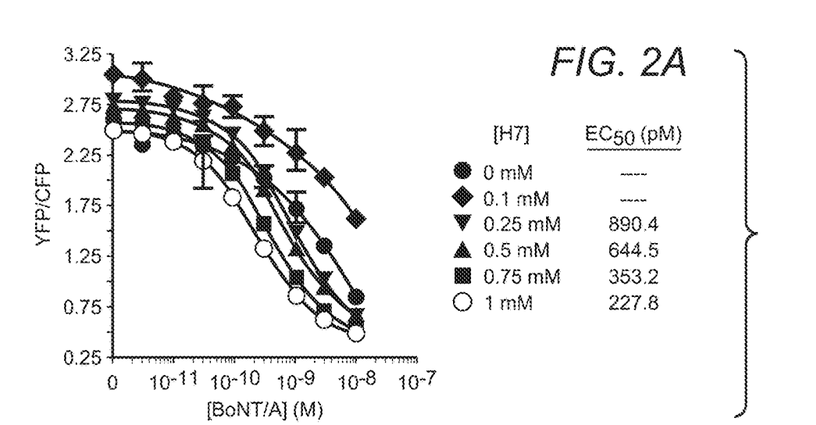
FIG. 2A shows the effect of H7 at different concentrations on the apparent EC50 of BoNT/A neurotoxin.
Figure 2B:
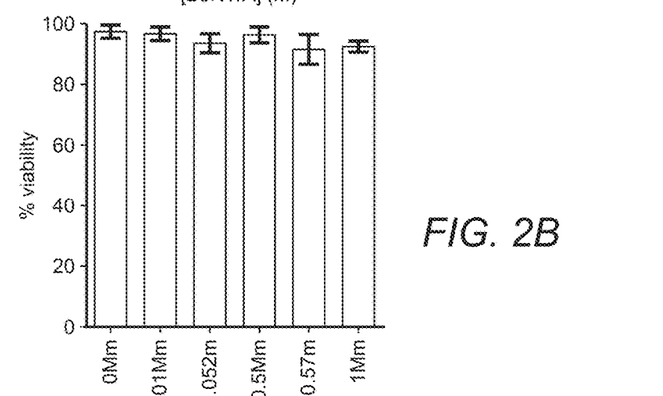
FIG. 2B shows a histogram of cell viability at different concentrations of H7.
Figure 3:
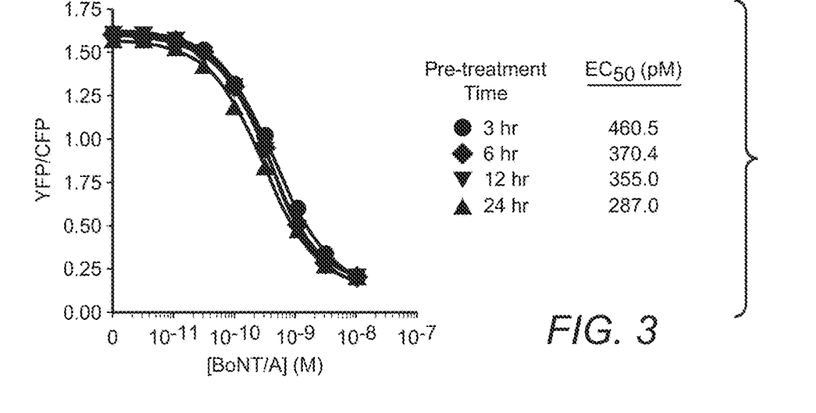
FIG. 3 is a graph showing that the effect of H7 pretreatment (before BoNT/A addition). Here, H7 is included with BoNT/A incubation as well.
Figure 4A:
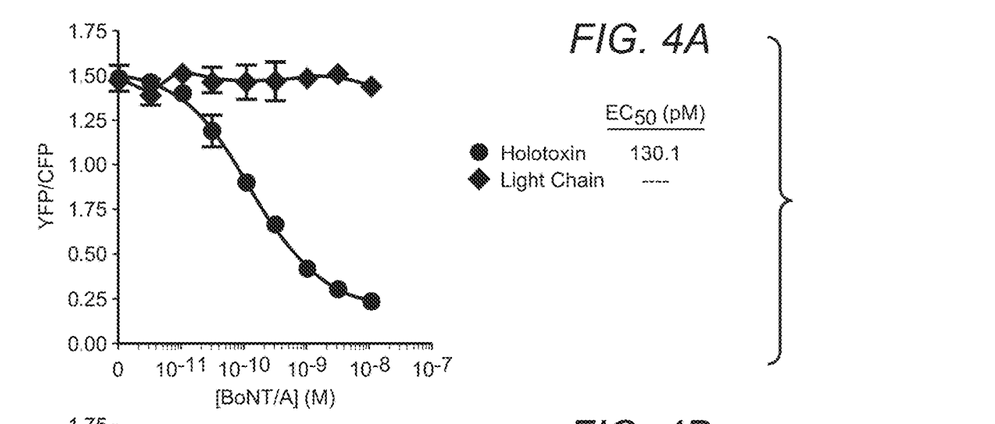
FIG. 4A shows the differential effects of intact holotoxin BoNT/A toxin and BoNT/A toxin light chain.
Figure 4B:
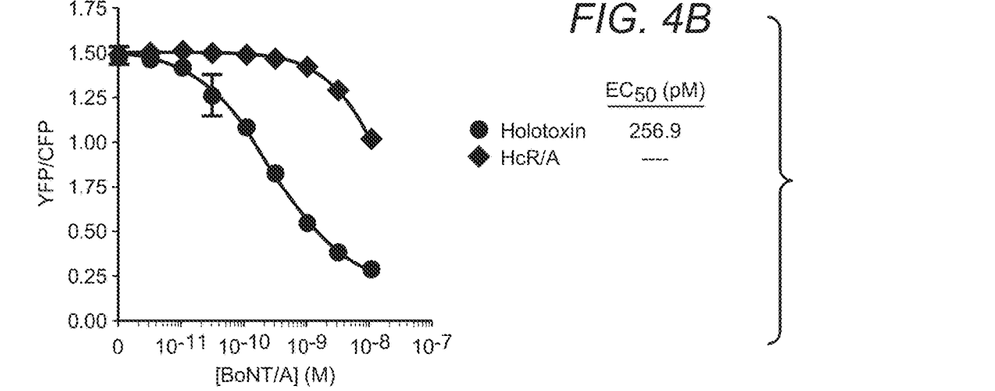
Figure 5:
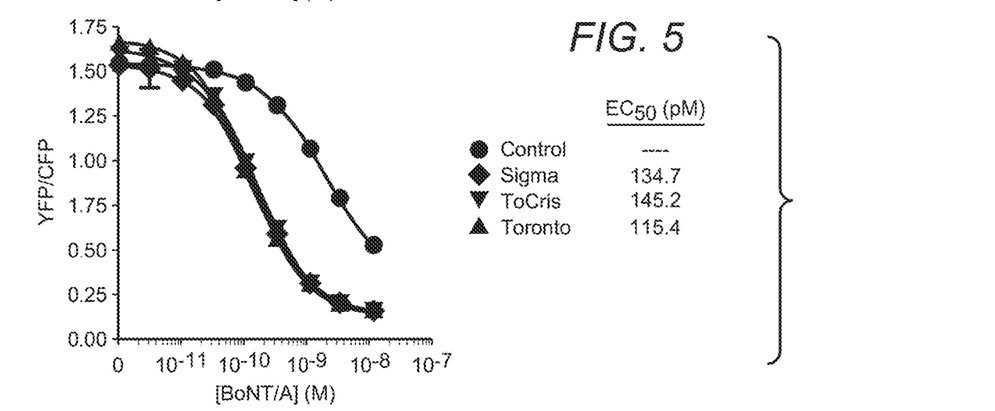
FIG. 5 is a graph showing that multiple H7 lots from different manufacturers all cause an increase in sensitivity. (There is a report in the literature that some H7 lots from certain manufacturers are not actually H7, thus we wanted to confirm the effect with multiple lots.)
Figure 6:
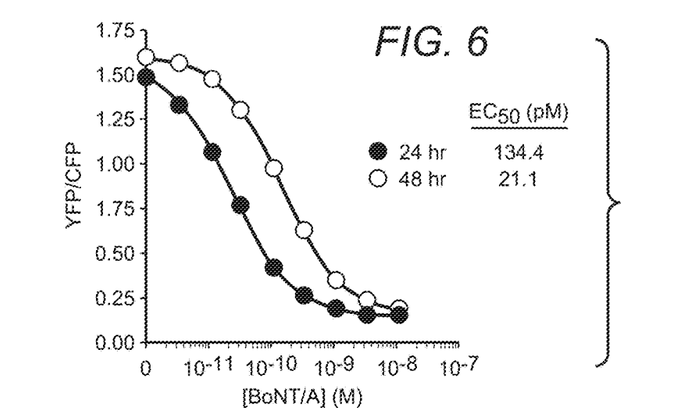
FIG. 6 is a graph showing assay response and sensitivity in the presence of H7 following a 24 and 48 hour incubation with BoNT/A. We expect that limits of detection of <3 pM will be possible with assay optimization.
Figure 7A:
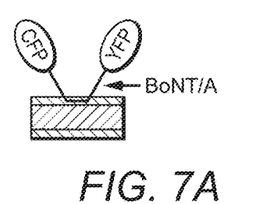
FIG. 7A is a schematic of a BoCell™ construct.
Figure 7B:
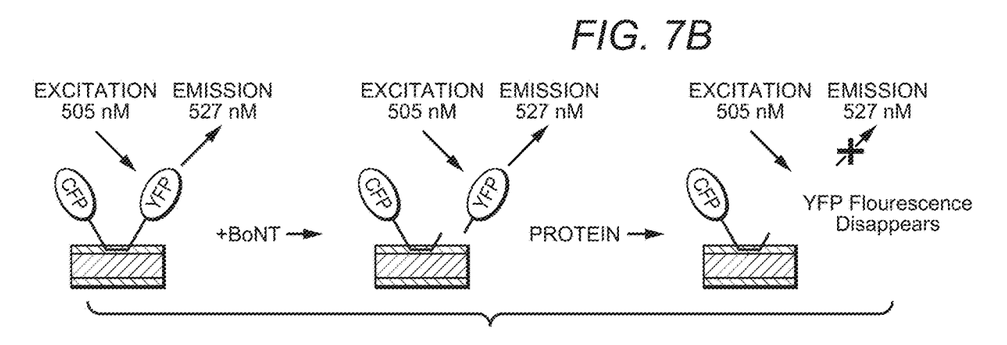
FIG. 7B is a schematic of an exemplary assay in which BoNT/A cell-based reporters are used to detect BoNT/A activity by loss of YFP fluorescence
Figure 8A:
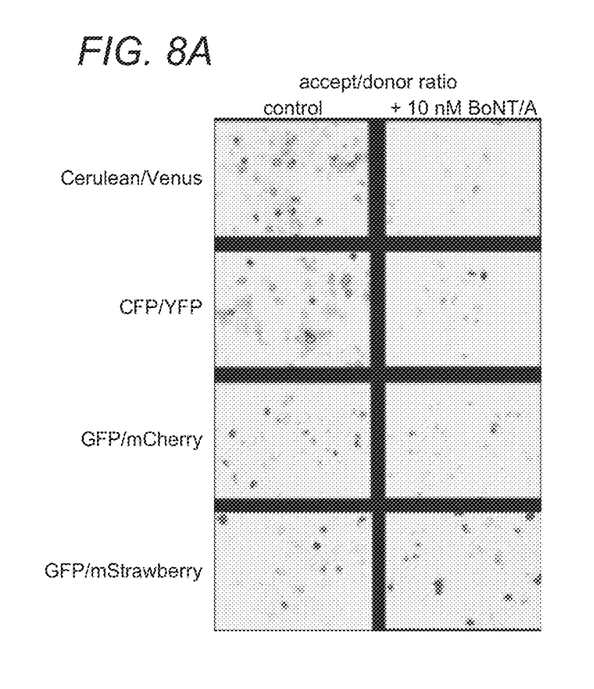
FIG. 8A is an image of BoNT/A-induced changes in fluorescence responses.
Figure 8B:
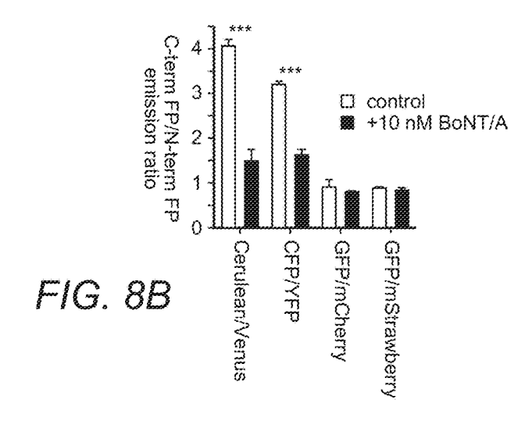
FIG. 8B is a chart showing fluorescence ratios and BoNT/A sensitivities of the cell-based reporters.
Figure 8C:
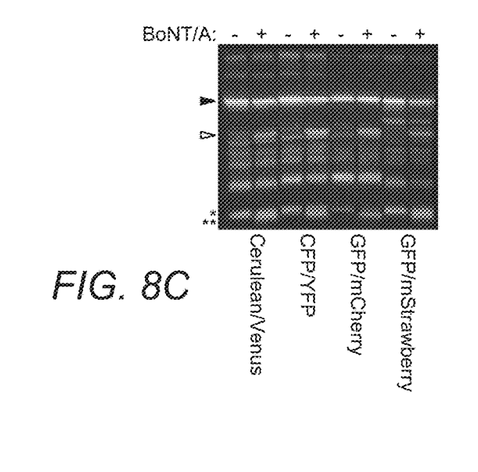
FIG. 8C is a blot showing activity of BoNT/A in cells regardless of the reporter.

In FIGS. 2A and 2B, A) BoCells were plated and pre-treated for 24 hr with the indicated concentration of H7. Control cells were treated with vehicle equivalent to the highest drug concentration tested. After pre-treatment. BoCells were treated with BoNT/A containing indicated drug concentration for an additional 24 hr. The assay response was collected by reading the emission forms of the reporters. Full-length (*) and cleaved (**) native SNAP-25 are indicated.

The inventive subject matter can be extended beyond cleavable substrates, to any assay having a construct with a reporter that can be de-protected, and then degraded in some manner by the cytosol or other local environment. For example, a susceptible reporter could be modified to include a 'bait' domain that is used to screen against a library of recombinant proteins that could possibly bind with the bait domain. Without the bait domain protected by a binding protein, the susceptible reporter will be degraded. In such an assay, cells expressing binding proteins will form a complex to protect the susceptible reporter from degradation, while cells expressing a binding partner to the bait will light up. The bait domain could advantageously be a small peptide, and the binding partners could be members of a library of proteins (or protein mutants). The system could also be reversed such that there is a library of bait domains tested against a single test protein (or test protein library).

In each of these instances it is considered advantageous to include a second reporter that is not degraded post-exposure by the cytosol or other local environment, or is at least degraded much more slowly post-exposure than the first reporter.

Still further, whereas the reporter can conveniently be selected from suitable fluorophores, it is contemplated that the reporter could be replaced or augmented by any other protein or other component with a defined function that is known to (a) have a relatively fast turnover in the cell without protection, and (b) that can be protected by interaction with a binding partner. Defined functions include transcription activators for reporter gene, repressors for lethal genes, etc (anything that can be easily identified or selected against).

Figure 9:
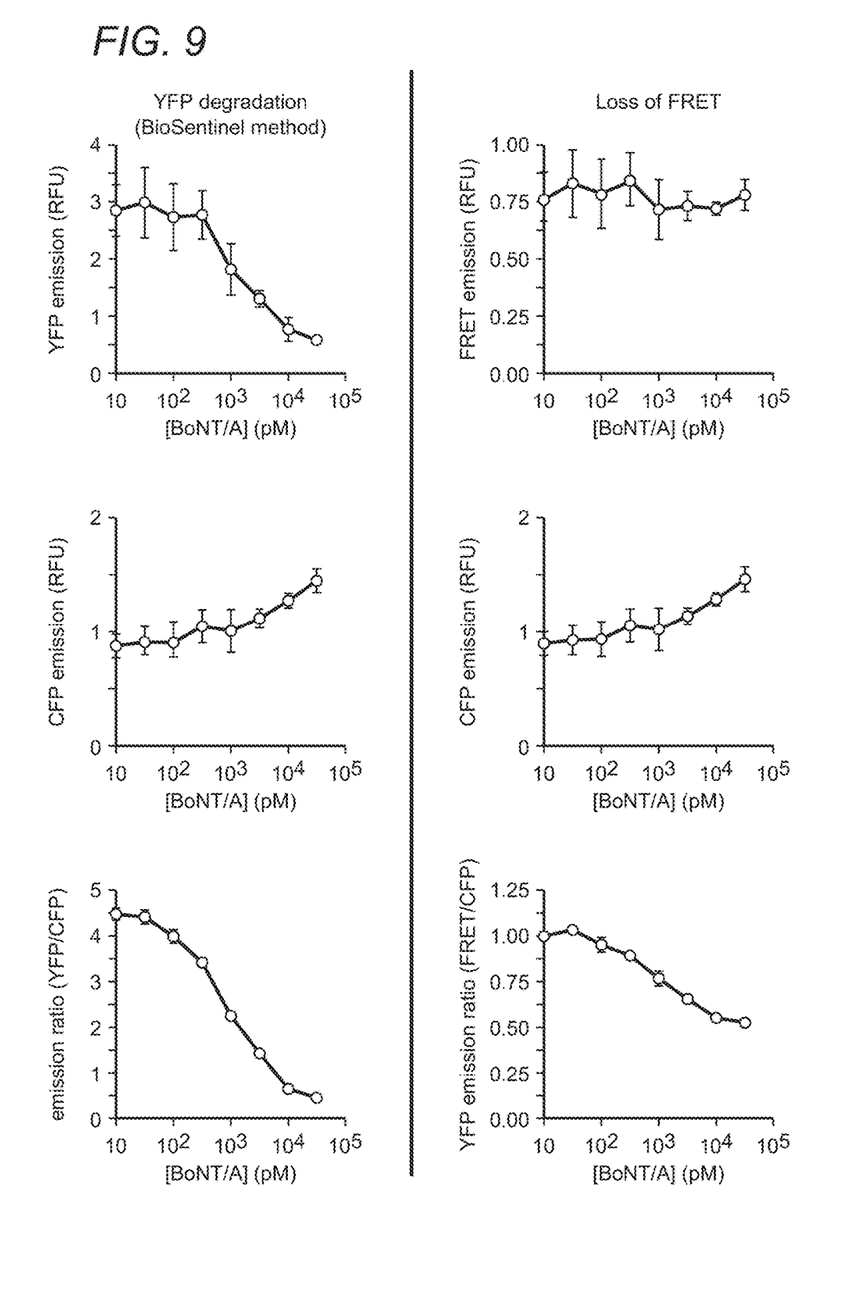
FIG. 9 comprises multiple charts showing emission data for both YFP degradation and loss of FRET according to the state of the art practice from the exact same plates of cells.

FIG. 9 comprises multiple charts showing emission data for both YFP degradation and loss of FRET according to the state of the art practice from the exact same plates of cells. For YFP degradation, directly and singularly excited YFP emissions (top, Ex500, Em526) and CFP emissions (middle, Ex434, Em470) are collected. Those emission are then background subtracted and the YFP emission is divided by CFP emission to control for cell density and reporter expression in the individual wells. That emission ratio (YFP/CFP, bottom) is then used for the essay report.

For loss of FRET, FRET emissions (top, Ex434, Em526) and CFP emissions (middle, Ex434, Em470) are collected. Those emissions are then background subtracted, and the FRET emission is divided by CFP emission to control for cell density and reporter expression in the individual wells. That emission ratio (FRET/CFP, bottom) is shown here to compare to the normal method.

The key comparison is the loss of directly excited YFP versus the loss of FRET emission. From the comparison between the measurements and the corresponding curves, it becomes immediately apparent that the overall dynamic range for YFP degradation is much larger than the dynamic range of loss of FRET emissions. In some cases, there is no difference, statistically, between cells treated with no BoNT versus sells treated with saturating concentrations of BoNT when looking solely at the raw FRET emissions. For the loss of FRET method, the BoNT dose response only becomes clear after dividing the FRET emission by the CFP (donor) emission. The CFP (donor) emission shows a small increase emission due to de-quenching in response to reporter cleavage.

In summary, the loss of FRET method reports BoNT-induced changes in the reporter very poorly, or not at all, and therefore cannot be therefore used for a correct qualitative and quantitative determination. In contrast, preferred methods contemplated herein have a high degree of specificity and reproducibility, which allow one to rely on the data for both the qualitative and quantitative analysis.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A composition for performing a cell based assay for Botulinum toxin, comprising:
   a cultured neuronal cell that is susceptible to intoxication by a Botulinum toxin; and a protein kinase C inhibitor at a concentration effective to generate, from the cultured neuronal cell, a sensitized cell, wherein the sensitized cell is characterized by an at least 0.5 log improvement in sensitivity to Botulinum neurotoxin intoxication in the cell based assay relative to the cultured neuronal cell prior to treatment with the protein kinase C inhibitor while retaining viability of the sensitized cell,
   wherein the protein kinase C inhibitor is an isoquinolynyl compound.

2. The composition of claim 1, wherein the isoquinolynyl compound is 1-(5-isoquinolinylsulfonyl)-2-methylpiperazine dichloride (H7).

3. The composition of claim 1, wherein the cultured cell is selected from a group consisting of a primary cultured neuron cell, PC12 cell or a derivative thereof, a primary cultured chromaffin cell, a neuroblastoma cell, a human adrenergic SK-N-SH cell, and a NS-26 cell line.

4. The composition of claim 1, further comprising a cell culture media optimized for contact with the protein kinase C inhibitor.

5. The composition of claim 1, further comprising Botulinum neurotoxin A, 0.05% human serum albumin, and 15.4 mM sodium chloride.

6. The composition of claim 1, further comprising Botulinum neurotoxin A, 0.0125% human serum albumin, and 0.25% lactose.

7. The composition of claim 1, further comprising Botulinum neurotoxin A, 0.1% human serum albumin, and 0.47% sucrose.

8. A kit comprising: the composition of claim 1.

9. The kit of claim 8, wherein the isoquinolynyl compound is 1-(5-isoquinolinylsulfonyl)-2-methylpiperazine dichloride (H7).

10. The kit of claim 8, wherein the cultured neuronal cell is selected from a group consisting of a primary cultured neuron cell, PC12 cell or a derivative thereof, a primary cultured chromaffin cell, a neuroblastoma cell, a human adrenergic SK-N-SH cell, and a NS-26 cell line.

11. The composition of claim 1, wherein the protein kinase C inhibitor is 1-(5-isoquinolinylsulfonyl)-2-methyl-piperazine dichloride (H7), and wherein the protein kinase C inhibitor is present at a concentration of from 0.25 mM to 1 mM.

* * * * *